United States Patent [19]

Najer et al.

[11] 3,950,345

[45] Apr. 13, 1976

[54] PROCESS FOR THE PREPARATION OF CIS-VINCAMINE
[75] Inventors: Henry Najer; Yves Robert Alain Pascal; Jean Pierre Gaston Lefevre, all of Paris, France
[73] Assignee: Synthelabo, Paris, France
[22] Filed: Feb. 21, 1975
[21] Appl. No.: 551,780

[30] Foreign Application Priority Data
Feb. 22, 1974   France .............................. 74.06051

[52] U.S. Cl. ..................... 260/293.52; 260/293.53
[51] Int. Cl.² ...................................... C07D 487/06
[58] Field of Search ............................... 260/293.52

[56] References Cited
OTHER PUBLICATIONS
Trojanek et al., Coll. Czech. Chem. Comm., 29, 433–446, (1964).

Primary Examiner—G. Thomas
Attorney, Agent, or Firm—Armstrong, Nikaido & Wegner

[57] ABSTRACT

A process is provided for the preparation of cis-vincamine by oxidising trans-vincamine with tertiary butyl hypochlorite to obtain dehydrovincamine chloride, reducing the dehydrovincamine chloride with a metal in an aqeous acidic medium and neutralising the product, and separating cis-vincamine from the resulting mixture of cis- and trans-vincamines. Cis-vincamine is useful for the treatment of circulatory disorders.

8 Claims, No Drawings

PROCESS FOR THE PREPARATION OF CIS-VINCAMINE

The present invention relates to a process for the preparation of cis-vincamine by isomerisation of the trans derivative. It is known that, of the two isomers, cis-vincamine possesses the stronger therapeutic activity and is therefore, in practice, the more useful and more interesting compound. Vincamine is a cerebral oxygenator and vasoregulator and may be used, for example, in the treatment of circulatory disorders.

The present invention provides a process for the preparation of cis-vincamine which process comprises:
a. oxidising trans-vincamine with tertiary butyl hypochlorite to obtain dehydrovincamine chloride of formula

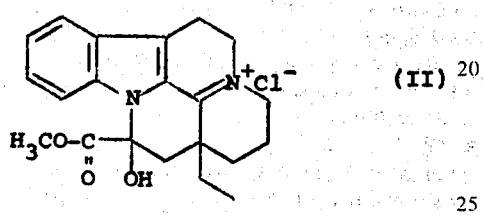

b. reducing the compound of formula (II) with a metal in an aqueous acidic medium and neutralising the product to obtain a mixture of cis- and trans-vincamines; and
c. separating cis-vincamine from the mixture.

The process of the invention is summarised by the following reaction scheme:

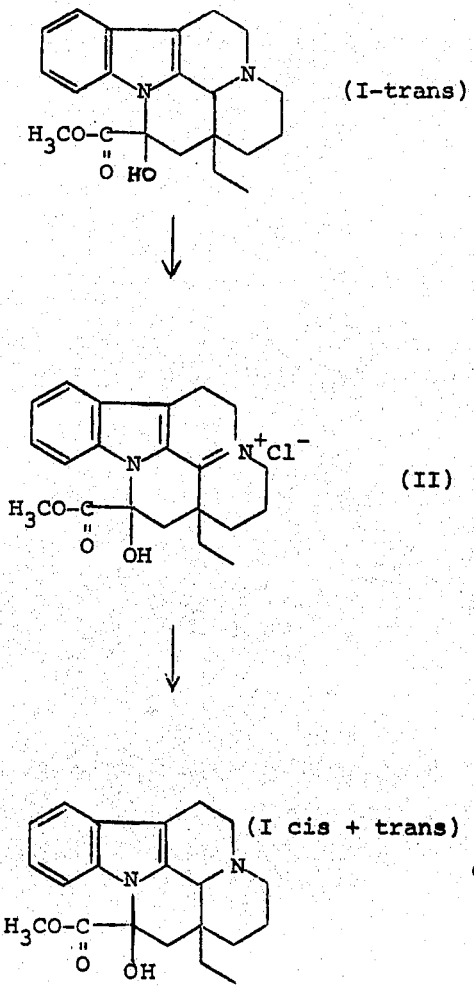

FIRST STAGE - FORMATION OF THE CHLORIDE OF DEHYDROVINCAMINE (II)

This compound (II) has already been described in the literature (Trojanek et al; Coll. Czch. Chem. Comm., 1964, 29, 433–446). It was prepared by dehydrogenation of vincamine using lead tetracetate, followed by treatment with hydrochloric acid. The chloride of dehydrovincamine was, however, recovered in an impure form and could not be conveniently purified.

It has now been found that if trans-vincamine is treated with tertiary-butyl hypochlorite in a solvent, it is possible to obtain the chloride of dehydrovincamine in excellent yield and in a very pure form.

SECOND STAGE - FORMATION OF CIS-VINCAMINE (I-cis)

It is generally believed that reduction of compounds of the eburnane type containing the structural unit (III)

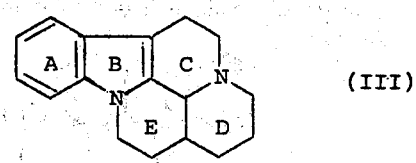

in which the ring E is opened gives a product of the cis-configuration. On the other hand, reduction of compounds in which the ring E remains intact gives a compound of trans-configuration. This has been confirmed for reductions with borohydrides.

It has unexpectedly been found that reduction of the chloride of dehydrovincamine (II) by means of a metal in an acidic aqueous medium, particularly with zinc and aqueous acetic acid, gives a mixture of cis- and trans-vincamines. The proportion of the cis compound obtained varies depending upon the relative proportions of water and acid used. On the other hand, if glacial acetic acid is used, only traces of the cis-isomer are obtained and there is a major proportion of the trans-isomer. The best yields of cis-vincamine are obtained for water: acetic acid ratios of 1:2 to 2:1 by volume. If the proportion of water in the mixture is increased, the amount of cis-vincamine obtained increases but because of vincamine's insolubility in water, the yield cannot exceed a certain limit.

The invention is illustrated by the following Example.

EXAMPLE

1. Chloride of Dehydrovincamine 3.6 Ml (1 equivalent) of tertiary butyl hypochlorite is added dropwise to a solution of 10g (28.2 mmoles) of trans-vincamine in a mixture of 225 ml of tetrahydrofuran and 25 ml of hexamethylphosphorotriamide without allowing the temperature to rise above 25°C. The mixture is shaken for an hour, the precipitate formed is separated, made into a paste, washed with ether and dried for 5 hours at 110°C under a vacuum of 20 mm. 10G (yield=91%) of the chloride of dehydrovincamine (containing 0.3% of water) are obtained; the melting point is 235°C.

2. Cis-vincamine

A solution of 2g (5.15 mmoles) of dehydrovincamine chloride in a mixture of 10 ml of acetic acid and 10 ml of water is refluxed and 4 g of zinc powder are added with shaking. The mixture is heated for 1 hour and filtered to remove excess zinc; the filtrate is diluted with 100 ml of water and neutralised with concentrated ammonia and the precipitated mixture of cis-vincamine and trans-vincamine is isolated. The precipitate is recrystallised from the minimum amount of benzene. 700 Mg (yield = 40%) of pure cis-vincamine (melting point = 262°C) are obtained.

3. Trans-vincamine

Trans-vincamine is obtained by evaporation of the benzene mother liquor from the recrystallisation. 700 Mg (yield = 40%) of the trans-isomer are obtained; this can be oxidised with tertiary butyl hypochlorite as described above and subjected to the rest of the process. This recycling can be carried out as many times as desired to give good yields of cis-vincamine.

We claim:
1. A process for the preparation of cis-vincamine, said process consisting essentially of the steps of
   a. oxidising trans-vincamine with tertiary butyl hypochlorite to obtain dehydrovincamine chloride of formula

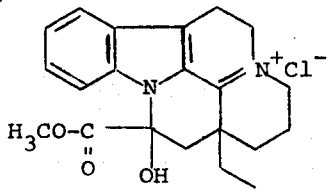

(II)

b. reducing the compound of formula (II) with a metal in an aqueous acidic medium and neutralising the product to obtain a mixture of cis- and trans-vincamines, and
   c. separating cis-vincamine from the mixture.
2. A process according to claim 1 in which the reduction in step (b) is carried out using zinc metal and a mixture of acetic acid and water.
3. A process according to claim 2 in which the ratio of water to acetic acid is 1:2 to 2:1 by volume.
4. A process according to claim 3 in which the ratio of water to acetic acid is 1:1 by volume.
5. A process according to claim 3 in which the ratio of water to acetic acid is 2:1 by volume.
6. A process according to claim 1, wherein in step (c), the cis-vincamine is separated from the mixture of cis-vincamine and trans-vincamine by fractional crystallisation.
7. A process according to claim 6 wherein the fractional crystallisation is effected in the minimum quantity of benzene.
8. A process according to claim 1 wherein the trans-vincamine remaining after the separation of the cis-vincamine in step (c) is recycled and the process repeated.

* * * * *